(12) United States Patent
Esnouf et al.

(10) Patent No.: US 10,039,869 B2
(45) Date of Patent: Aug. 7, 2018

(54) PORTABLE SUCTION DEVICE

(71) Applicant: CONSTRUCT MEDICAL PTY LTD, Woodend, VIC (AU)

(72) Inventors: Philip Stuart Esnouf, Richmond (AU); David John Auld, Ringwood East (AU)

(73) Assignee: Construct Medical Pty, Ltd., Woodend (AU)

( * ) Notice: Subject to any disclaimer, the term of this patent is extended or adjusted under 35 U.S.C. 154(b) by 363 days.

(21) Appl. No.: 14/442,649

(22) PCT Filed: Nov. 13, 2013

(86) PCT No.: PCT/AU2013/001308
§ 371 (c)(1),
(2) Date: May 13, 2015

(87) PCT Pub. No.: WO2014/075133
PCT Pub. Date: May 22, 2014

(65) Prior Publication Data
US 2016/0279305 A1  Sep. 29, 2016

(30) Foreign Application Priority Data

Nov. 13, 2012  (AU) ................. 2012904939

(51) Int. Cl.
*A61M 1/00* (2006.01)
*A61M 16/04* (2006.01)

(52) U.S. Cl.
CPC ........ *A61M 1/0076* (2013.01); *A61M 1/0074* (2013.01); *A61M 1/0001* (2013.01); *A61M 16/0463* (2013.01); *A61M 2210/1025* (2013.01)

(58) Field of Classification Search
CPC .............. A61M 1/0076; A61M 1/0074; A61M 16/0463; A61M 1/0052; A61M 1/005;
(Continued)

(56) References Cited

U.S. PATENT DOCUMENTS 4,790,818 A    12/1988  DeLuca et al.
5,385,851 A     1/1995  McKinnon, Jr. et al.
(Continued)

FOREIGN PATENT DOCUMENTS

CN    2058850 U    7/1990
CN    2746914 Y   12/2005
(Continued)

OTHER PUBLICATIONS

International Search Report dated Jan. 29, 2014 (PCT/AU2013/001308); ISA/AU.

*Primary Examiner* — Ariana Zimbouski
(74) *Attorney, Agent, or Firm* — Banner & Witcoff, Ltd.

(57) ABSTRACT

A portable suction device comprising: a gas inlet for receiving pressurized gas from an enclosed source; a gas flow path that extends from the gas inlet to an exhaust; a suction generator that has a suction inlet, the gas flow path extending through the suction generator, such that gas flow through the flow path generates a low pressure at the suction inlet; a collection container with a collection inlet and an outlet that is coupled to the suction inlet; a suction tube that has proximal and distal ends, the proximal end being connected to the collection inlet of the collection container; a valve for controlling gas flow through the flow path, the valve having a stem that is configured to pierce the source with movement of the valve from a closed position.

22 Claims, 7 Drawing Sheets

(58) Field of Classification Search
CPC .............. A61M 1/0031; A61M 1/0001; A61M 2210/1025
See application file for complete search history.

(56) References Cited

U.S. PATENT DOCUMENTS

2010/0241026 A1    9/2010  Boukas
2012/0157911 A1*   6/2012  Rooks .................. A61B 18/042
                                              604/26

FOREIGN PATENT DOCUMENTS

| CN | 201692380 U   | 1/2011 |
| WO | 2003009766 A1 | 2/2003 |
| WO | 2012058720 A1 | 5/2012 |

* cited by examiner

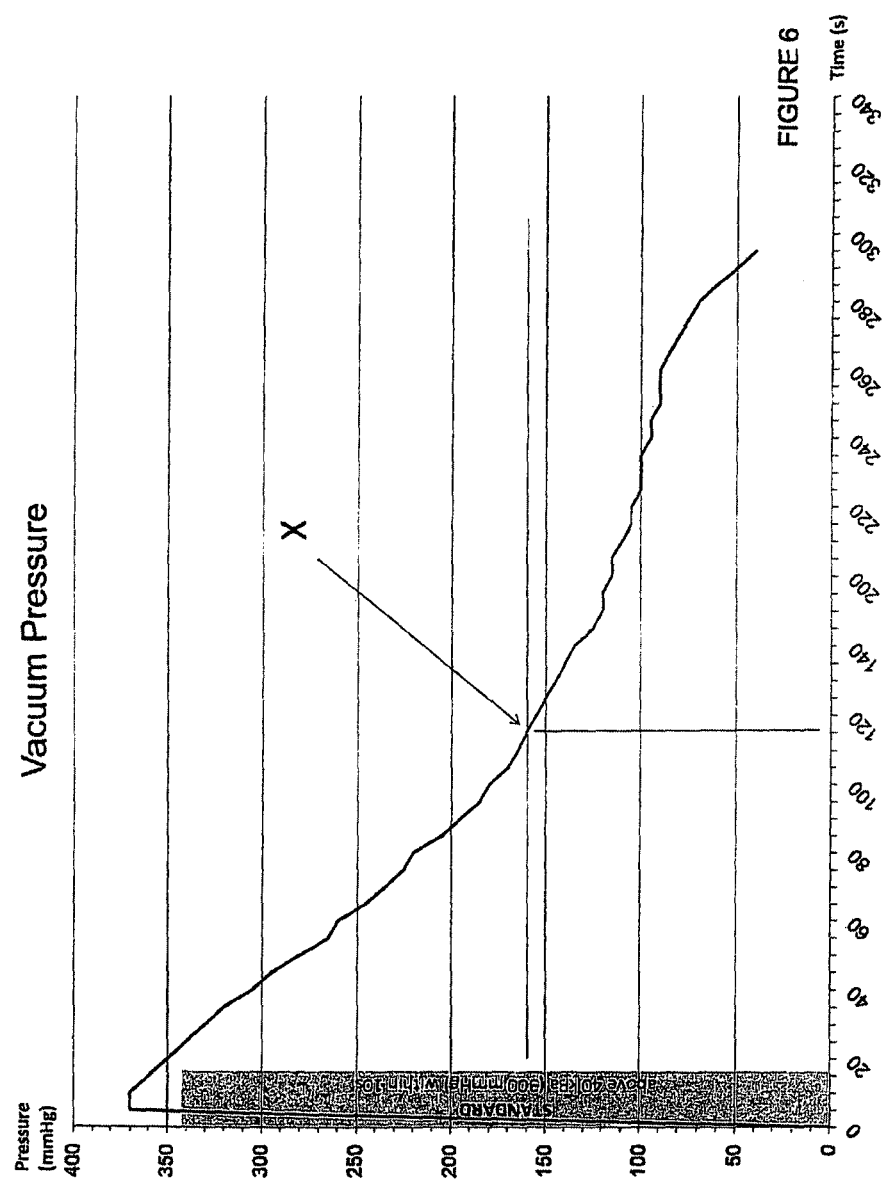

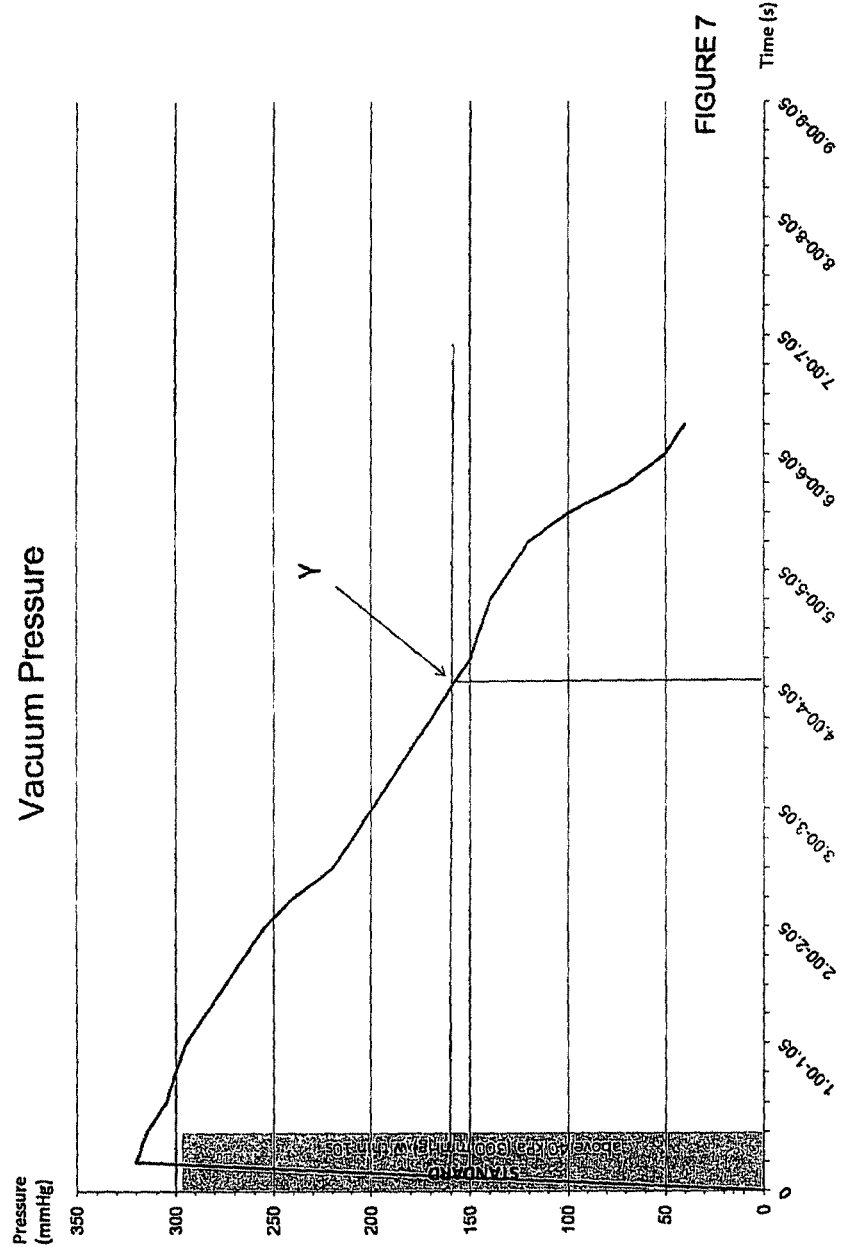

PORTABLE SUCTION DEVICE

CROSS-REFERENCE TO RELATED APPLICATIONS

This application is a national stage application of co-pending PCT application PCT/AU2013/001308 filed Nov. 13, 2013. The disclosure of this application is expressly incorporated herein by reference in its entirety.

FIELD OF THE INVENTION

This invention relates to a portable suction device.

BACKGROUND

Portable hand held suction devices are used in first aid and medical applications for clearing the airway of a person who is suffering from trauma, injury or other medical condition in which the person's airway is or could be blocked. In circumstances requiring use of such devices, the first aider often needs to have the device operative immediately to enable effective cardiopulmonary resuscitation to proceed with minimum delay.

One device of this type is disclosed in International Application No. PCT/AU201/001408 filed in the name of the present applicant the disclosure of which is incorporated herein by reference.

Furthermore, devices of this type may need to reliably provide suction of at least 40 kPa below atmospheric pressure for at least 10 seconds. However, suction in the range of 40 kPa to 60 kPa below atmospheric pressure is desirable. Furthermore, providing reliable suction for longer periods is an advantage in case the device needs to be used for an extended period, or used repeatedly.

Accordingly, it is desired to address the above, and/or at least provide a useful alternative.

SUMMARY OF THE INVENTION

The present invention provides a portable suction device comprising:

a gas inlet for receiving pressurized gas from an enclosed source;

a gas flow path that extends from the gas inlet to an exhaust;

a suction generator that has a suction inlet, the gas flow path extending through the suction generator, such that gas flow through the flow path generates a low pressure at the suction inlet;

a collection container with a collection inlet and an outlet that is coupled to the suction inlet;

a suction tube that has proximal and distal ends, the proximal end being connected to the collection inlet of the collection container;

a valve for controlling gas flow through the flow path, the valve having a stem that is configured to pierce the source with movement of the valve from a closed position.

The stem may have a pointed tip to pierce the source. The tip may have one or more passages to allow gas to flow through the tip and into the gas flow path.

In some embodiments, the source is a capped metal cylinder, and the stem is configured to pierce the cap.

The device can include an actuator and the valve includes a spindle, wherein the actuator bears on the spindle to open the valve.

The spindle co-operates with the stem, such that initial movement of the actuator causes the stem to pierce the source.

The device can include a filter in the gas flow path between the valve and the suction generator. In one embodiment, the filter may be made of a sintered material. In some alternative embodiments, the filter may be a mesh.

Preferably, the portable suction device further has a body within which the source is retained.

Preferably, the cylinder has a neck with an external thread, and the cap covers an opening in the neck, and the body includes an internal thread to receive the external thread of the cylinder.

The present invention also provides a portable suction device comprising:

a gas inlet for receiving pressurized gas from an enclosed source that has a neck that is receivable in the gas inlet and a side wall;

a gas flow path that extends from the gas inlet to an exhaust;

a suction generator that has a suction inlet, the gas flow path extending through the suction generator, such that gas flow through the flow path generates a low pressure at the suction inlet;

a collection container with a collection inlet and an outlet that is coupled to the suction inlet;

a suction tube that has proximal and distal ends, the proximal end being connected to the collection inlet of the collection container;

a sleeve that is to extend around the side wall of the source, whereby heat is conducted from the sleeve to the source as pressurized gas is discharged from the source.

Preferably, the sleeve is made of a material having a high volumetric heat capacity. Alternatively or additionally, the sleeve is made of a material having a high thermal conductivity.

In one embodiment, the sleeve is made of a material containing copper in an elastomeric matrix.

The present invention also provides a portable suction device comprising:

a gas inlet for receiving pressurized gas from an enclosed source that has a neck that is receivable in the gas inlet, a side wall, and a base;

a gas flow path that extends from the gas inlet to an exhaust;

a suction generator that has a suction inlet, the gas flow path extending through the suction generator, such that gas flow through the flow path generates a low pressure at the suction inlet;

collection container with a collection inlet and an outlet that is coupled to the suction inlet;

a suction tube that has proximal and distal ends, the proximal end being connected to the collection inlet of the collection container;

wherein the source is disposed in the gas flow path such that at least a portion of the gas discharged from the suction generator is directed along the side wall of the source prior to exiting the device.

The device can include a shroud with an internal space within which the source is disposed in use of the device, the internal space forming part of the gas flow path.

Preferably, the shroud has an exhaust end that forms the exhaust of the gas flow path.

Preferably, the shroud projects past the base of the source.

In some embodiments, the shroud forms a handle for a user to hold the device during use.

The device can include a sleeve that extends around the side wall of the source. The device can be configured such that gas discharged from the suction generator is to pass between the sleeve and the source, and/or between the sleeve and the shroud.

The sleeve can extend around a portion of the base, and include an aperture through which gas can exit the sleeve.

BRIEF DESCRIPTION OF THE DRAWINGS

In order that the invention may be more easily understood, embodiments will now be described, by way of example only, with reference to the accompanying drawings, in which:

FIG. 6 is a graph showing pressure reduction over time during continuous operation of the portable suction device of FIG. 1; and FIG. 7 is a graph showing pressure reduction over time during intermittent operation of the portable suction device of FIG. 1.

DETAILED DESCRIPTION

Figure 1:
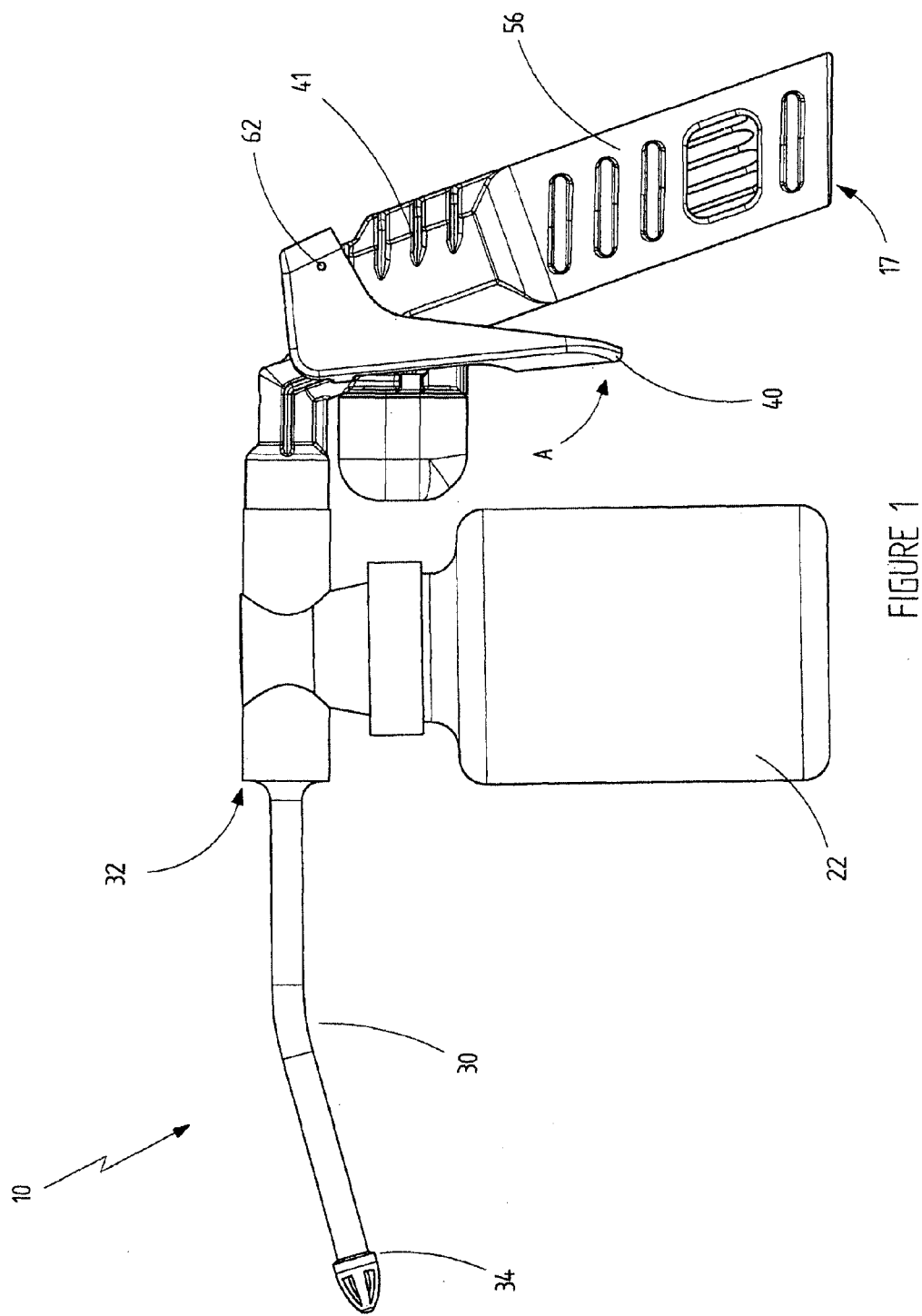
FIG. 1 is a side elevation view of a portable suction device according to an embodiment of the present invention.
Figure 2:
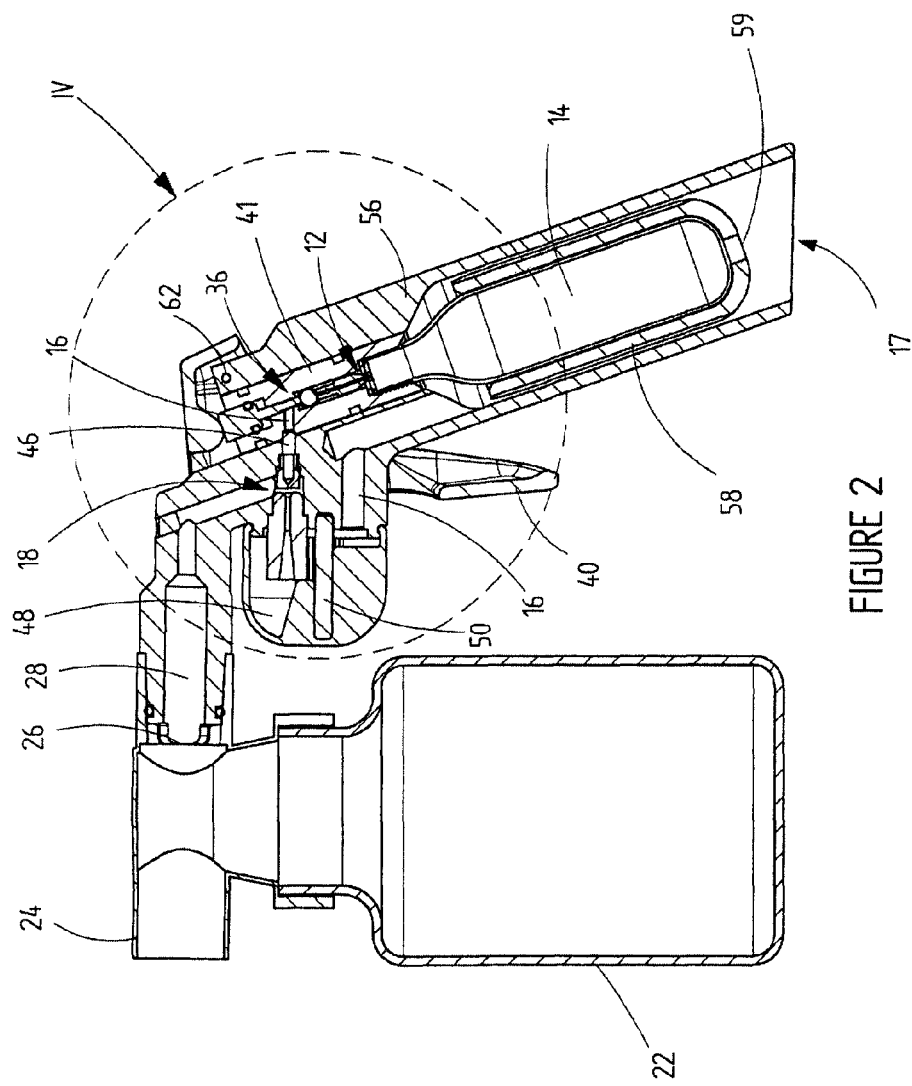
FIG. 2 is a vertical cross section view of the portable suction device of FIG. 1.
Figure 3:
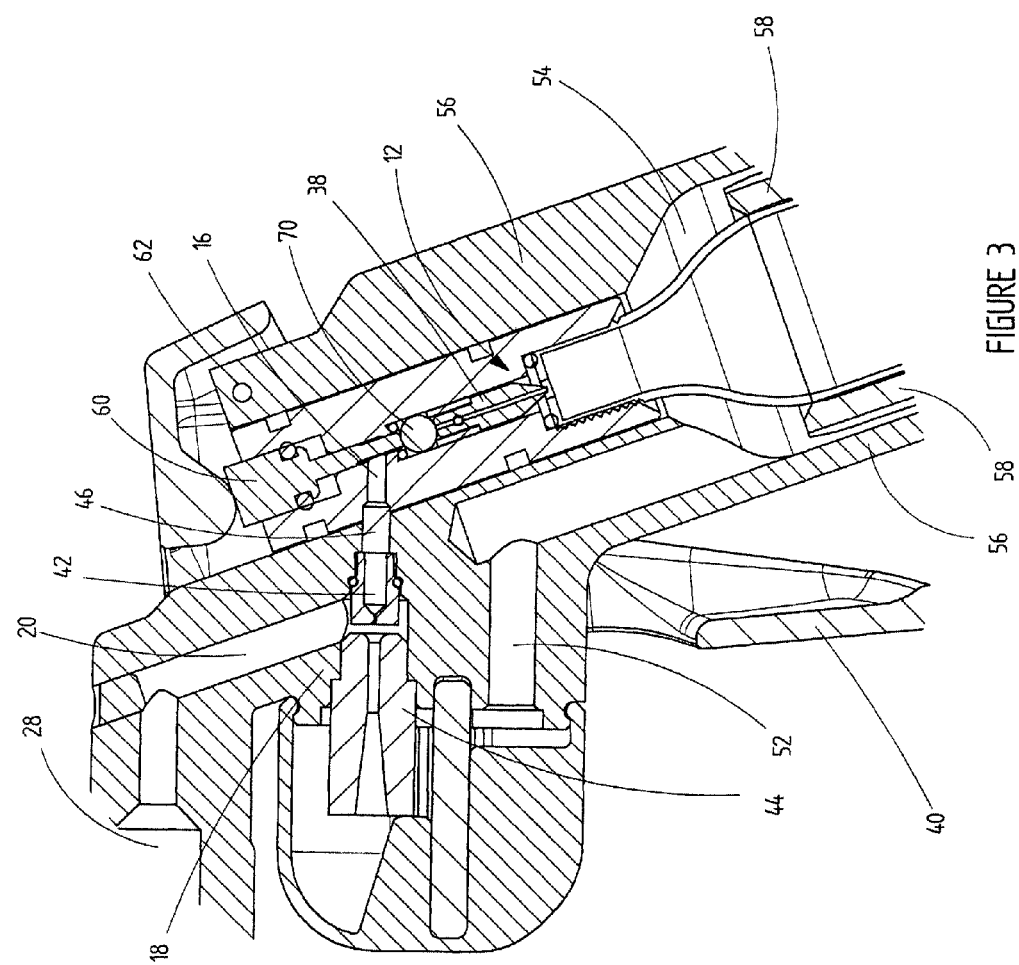
FIG. 3 is a simplified schematic cross section view of a valve of the portable suction device of FIG. 1, showing the actuator in a closed position.

FIGS. 1 to 3 show a portable suction device 10 according to a first embodiment. The device 10 has a gas inlet 12 that is to receive pressurized gas from an enclosed source. In this particular embodiment, the source is a cartridge 14 that contains liquefied gas. In this particular embodiment, the liquefied gas is carbon dioxide. This type of cartridge is often referred to as a $CO_2$ cartridge, a $CO_2$ bulb, or a $CO_2$ cylinder.

A gas flow path 16 extends from the gas inlet 12 to an exhaust 17. Further, the flow path 16 extends through a suction generator 18 having a suction inlet 20. Thus, a gas flow through the flow path 16 generates a low pressure at the suction inlet 20.

The device 10 also has a collection container 22 with a collection inlet 24 and an outlet 26 that is coupled to the suction inlet 20 via a passageway 28. A suction tube 30, with a proximal end 32 and a distal end 34, is provided. The proximal end 32 is connected to the collection inlet 24 of the collection container 22.

Further, the device 10 has a valve 36 for controlling gas flow through the flow path 16. The valve 36 has a stem 38 that is configured to pierce the source with movement of the valve from a closed position. The features of the valve 36 are discussed in further detail in connection with FIGS. 3 to 5.

The device 10 has an actuator, which in this embodiment is in the form of a trigger 40. In use, an operator pulls the trigger 40 (in the direction indicated by arrow A in FIG. 1), which opens the valve 36 to allow pressurized gas to be discharged from the cartridge 14 into the flow path 16. While gas is flowing through the flow path 16, a negative pressure is developed at the distal end 34 of the suction tube 30, which can be used to suck liquids from a person's airway in preparation for cardiopulmonary resuscitation. Liquids that are sucked through the suction tube 30 can be collected in the container 22 without impeding the continued operation of the device 10.

As shown in FIGS. 2 and 3, the suction generator 18 has a jet 42 with a small diameter orifice. Pressurized gas is discharged from the jet 42 into a cone 44, which defines a bore having an initial portion of constant diameter and a second portion that is conical. The exit of the jet 42, and the opening of the cone 44 are spaced apart. The gas pressure downstream of the jet 42 is lower than atmospheric pressure, which enables a negative pressure (relative to atmospheric pressure) to be generated in the passageway 28.

The tube of the jet 42 has a diameter that is in the range of approximately 0.8 mm to 0.25 mm. To prevent particulates clogging the tube of the jet 42, a filter 46 is provided at the opening of the jet 42. In this embodiment, the filter is made of a sintered material.

Downstream of the suction device 18, the gas flow path 16 has a chamber 48, a filter 50, and a passageway 52 that opens into an internal space 54 defined by a shroud 56. The shroud 56 is formed as part of the body 41. As shown in FIG. 2, in use of the device 10, the cartridge 14 is disposed in the shroud 56. The shroud 56 has an exhaust end that forms the exhaust 17 of the gas flow path 16. Thus, at least a portion of the gas discharged from the suction generator 18 is directed along the side wall of the cartridge 14 prior to exiting the device 10. In this particular embodiment, all the gas discharged from the suction generator 18 is directed along the entire length of the side wall of the cartridge 14 prior to exiting the device.

The gas discharged from the suction generator 18 is a mixture of gas discharged from the cartridge 14 and ambient air that has been drawn into the suction generator 18 through the suction tube 30 and/or collection container 22. Directing the gas flow along the side wall of the cartridge 14 results in heat being transferred to the cartridge 14, and thus to the contents of the cartridge 14. Accordingly, this heat transfer reduces the temperature drop within the cartridge 14 that occurs during discharge of gas from the cartridge 14. As a consequence, the pressure drop is also minimized, which improves the performance of the device 10.

As shown in FIG. 2, the shroud 56 projects past the base of the cartridge 14. Furthermore, the shroud 56 forms a handle for a user to hold the device during use.

The device 10 also has a sleeve 58 that is to extend around the side wall of the cartridge 14. As the cartridge 14 cools during discharge of gas, heat is conducted from the sleeve 58 to the cartridge 14.

The sleeve 58 is made of a material having a high volumetric heat capacity. In this particular embodiment, the sleeve 58 is made of a material having a high thermal conductivity, such a material containing copper in an elastomeric matrix.

As will be appreciated, prior to use the cartridge 14 and sleeve 58 are at approximately the same temperature. Thus, heat can readily be transferred from the sleeve 58 to cartridge 14, which reduces the temperature drop and thus pressure drop in the cartridge 14 during discharge, which improves the performance of the device 10.

The device 10 is configured such that gas discharged from the suction generator 18 is to pass between the sleeve 58 and the cartridge 14, and/or between the sleeve 58 and the shroud 56.

As shown in FIG. 2, the sleeve 58 extends around a portion of the base of the cartridge 14, and includes an aperture 59 through which gas can exit the sleeve 58.

Figure 4:
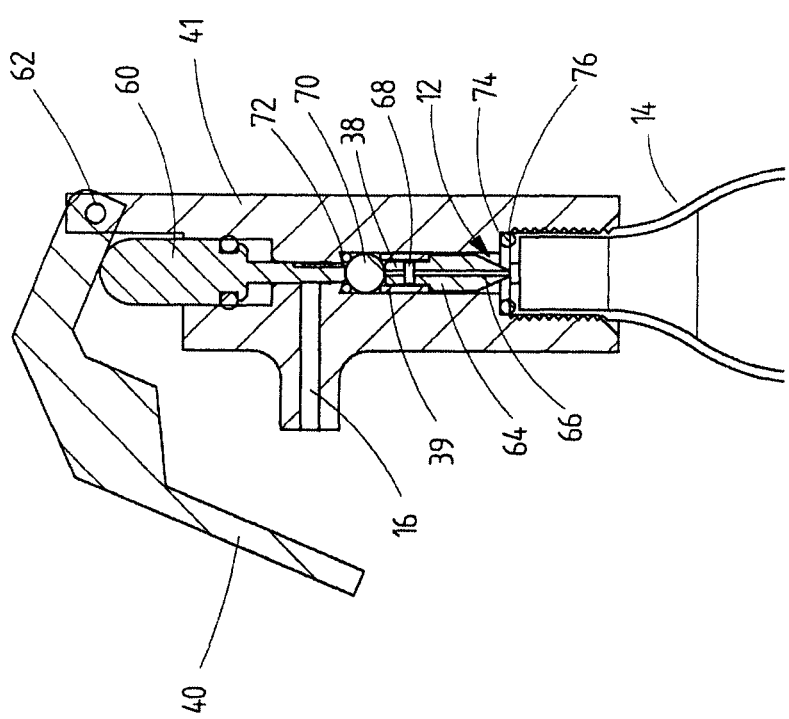
FIG. 4 is an enlarged view of region IV in FIG. 3.
Figure 5:
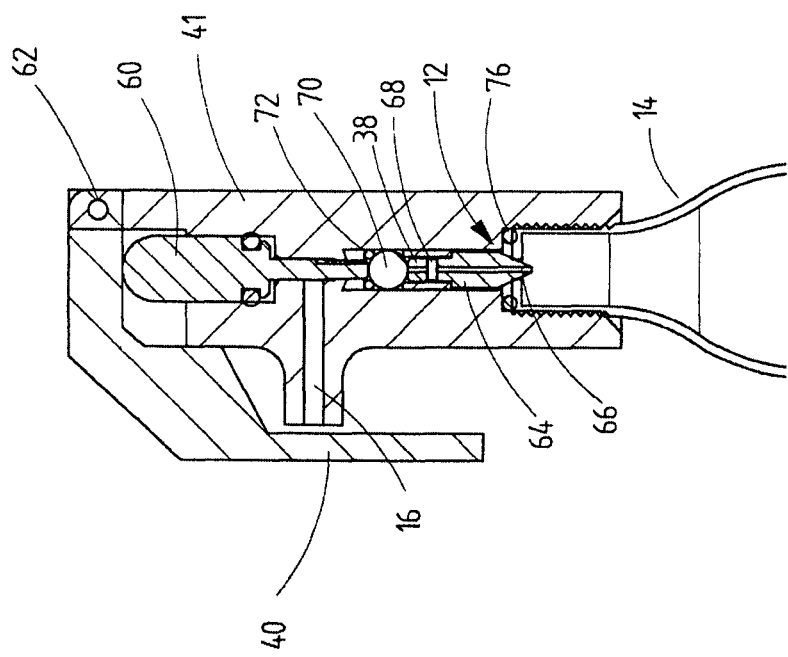
FIG. 5 is a schematic cross section view of the valve of FIG. 3, showing the actuator in an open position.

FIGS. 4 and 5 show a simplified schematic cross section view of the valve 36 of the suction device 10. In FIG. 4 the trigger 40 is shown in a position that corresponds with the valve 36 being closed, and in FIG. 5 the trigger 40 is shown in a position that corresponds with the valve 36 being open. The device 10 includes a body 41 that defines part of the gas flow path 16, and within which the valve 36 is disposed. Furthermore, the suction generator 18 is disposed within the body 41.

The stem 38 has a pointed tip 64 that is shaped to pierce the cap of the cartridge 14. The valve 36 includes a spindle 60, and the trigger 40 bears on the spindle 60 to open the valve 36. The trigger 40 rotates on a pivot 62 between the closed and open positions. The spindle 60 is positioned close to the pivot 62, and thus the trigger 40 has a mechanical advantage that that facilitates the stem 38 piercing the cartridge 14.

The tip 64 has a transverse passage 66 that extends transversely through the stem 38, and a longitudinal passage 68 that extends longitudinally from the leading end of the tip 64. The longitudinal passage 68 opens into the transverse passage 66 such that gas can flow through the tip 64, and continue into and/or through the gas flow path 16.

As shown most clearly in FIG. 4, the cartridge 14 has a cap that is pierced by the stem 38. As will be apparent from FIGS. 3 to 5, the initial movement of the trigger 40 from the closed position causes the valve 36 to move from the closed position, and in doing so causes the stem 38 to pierce the cap of the cartridge 14.

A ball 70 is disposed between the stem 38 and the spindle 60. The ends of each of the stem 38 and spindle 60 that face the ball 70 are concave, and thus the ball 70 helps to transfer movement between the stem 38 and spindle 60. An O-ring 72 is disposed about the spindle 60 adjacent the ball 70. When the valve 36 is in the closed position, the O-ring 72 is compressed between the ball 70 and a shoulder 74 in the body 41, thus preventing gas flowing through the flow path 16.

The end of the spindle 60 that is adjacent the ball 70 is disposed in the flow path 16. The spindle 60 is shaped such that when the valve 36 is in an open position, gas is able to flow around that part of the spindle 60 and continue along the flow path 16.

Upon release of the trigger 40, the stem 38 can remain embedded in the cap of the cartridge 14. The valve 36 includes a spring 39 (shown in FIGS. 4 and 5) that extends around the stem 38. Upon release of the trigger 40, the spring urges the ball 70 and the spindle 60 away from the stem 38, which causes the valve 36 to close and seal.

As shown in FIGS. 2 to 5, the cartridge 14 is retained within the body 41. To this end, the cartridge 14 has a neck with an external thread, and the body 41 has an internal thread that is to receive the external thread of the cartridge 14. A large O-ring 76 is provided to be compressed between the cap of the cartridge 14 and the body 41 to form a seal that prevents gas leaking from the cartridge 14 into the internal space defined by the shroud 56.

The suction tube 30 has a length that readily permits oro-pharyngeal suction in adults. Further, the suction tube 30 has a length that could reach the pharynx and, if necessary, to the epiglottis in an adult patient. This has the advantage of enabling the collection container 22 to be as close to the distal end 34 of the suction tube 30 as possible, which allows suction to be generated quickly at the patient interface when the trigger 40 is squeezed to open the valve 36.

The suction tube has a length that is within the range of 100 mm to 280 mm. In this particular embodiment, the suction tube 30 is approximately 150 mm in length.

Furthermore, the overall construction of the device 10 allows the entire device to be between the operator and the patient in use. This enables the operator to work the device 10 with minimal distraction from the patient, as in use the entire device is likely to be in the field of view of the operator. Consequently, the likelihood of successful cardio-pulmonary resuscitation is increased.

In preferred embodiments, the portable suction device is a single piece unit that is constructed to inhibit disassembly. To this end, the suction tube 30 is securely attached to the collection inlet 42 of the collection container 22, and the portion of the body 41 that defines the passageway 28 is securely attached to the outlet 26 of the collection container 22. Accordingly, the device is intended for single use only. Thus, both the suction tube 20 and the body 41 are secured to the collection container 22. Furthermore, the cartridge is intended to be installed when the device is provided to users. The inability to re-use the device is considered desirable in light of the fact that, when used as intended, bodily fluids are likely to be drawn through the suction tube and into the collection container.

Furthermore, the cartridge has a long shelf-life, and thus the device can remain unused for an extended period without compromising the performance of the device. Accordingly, embodiments of the portable suction device can provide a handheld, single use device that is not readily disassembled.

$CO_2$ has the advantage that it can be liquefied at relatively low pressures, and provides a large volumetric supply within a compact container. However, in some alternative embodiments, the cartridge can contain substances other than $CO_2$ that are similarly of low combustibility and/or are relatively inert in atmospheric conditions. In some examples, the substance may be nitrous oxide, nitrogen, noble gases (such as helium or argon), air. The substance may also be blends of such substances.

The cartridge does not contain hydrocarbons or refrigerants.

In some alternative embodiments, the sleeve can be made of other materials that have a high volumetric heat capacity, such as aluminum, steel, silver, and iron. Such materials can be provided in combination, and/or in a blended material with plastics, elastomers, or the like.

FIG. 6 is a graph showing pressure reduction (on the vertical axis) over time (on the horizontal axis) during continuous operation of a portable suction device according to an embodiment of the present invention. The units on the vertical axis show the pressure reduction from atmospheric pressure in millimeters of mercury (mmHg); the units on the horizontal axis show time in seconds.

As shown in FIG. 6, the suction device is capable of providing approximately 375 mmHg pressure reduction within approximately 8 seconds, which exceeds an international standard requiring devices of this type be able to achieve a pressure reduction of 300 mmHg (approximately 40 kPa) within 10 seconds of continuous operation.

In addition, an international standard requires that devices of this type be capable of a minimum pressure of 160 mmHg for use in pharyngeal suction. The graph shows that the suction device provides a pressure reduction of in excess of 160 mmHg for approximately 117 seconds (point X indicated in FIG. 5).

FIG. 7 is a graph showing pressure reduction (on the vertical axis) over time (on the horizontal axis) during intermittent operation of a portable suction device according to an embodiment of the present invention. The units on the vertical axis show the pressure reduction from atmospheric pressure in millimeters of mercury (mmHg); the units on the horizontal axis show time in seconds.

In generating the data for FIG. 7, the suction device was repeatedly operated with the valve open for 5 seconds and then closed for 10 seconds. This intermittent operation mimics use of the device in a clinical setting, in which the device is likely to be used in short bursts.

As shown in FIG. 7, at the conclusion of the initial 5 second period of operation, the suction device achieved a pressure reduction of approximately 320 mmHg, which also exceeds an international standard requiring devices of this type be able to achieve a pressure reduction of 300 mmHg (approximately 40 kPa) within 10 seconds of continuous operation.

In addition, the graph of FIG. 7 shows that the suction device in this test was able to provide a pressure reduction of in excess of 160 mmHg for approximately 17 cycles (point Y indicated in FIG. 7). This corresponds with approximately 4 minutes of intermittent use according to the test cycle.

Further tests have shown that a portable suction device according to embodiments of the present invention are able to evacuate 200 mL of simulated vomit in less than 10 seconds, which meets an international standard for devices of this type.

The device 10 illustrated in FIG. 1 has an ergonomical efficiency that facilitates the operator switching the suction on and off rapidly by simply working the trigger 40.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A portable suction device comprising:
    a body;
    a cartridge of liquefied carbon dioxide, the cartridge including a cap;
    the body including a gas inlet for receiving pressurized carbon dioxide from the cartridge;
    a gas flow path that extends from the gas inlet to an exhaust;
    a suction generator that has a suction inlet, the gas flow path extending through the suction generator, such that gas flow through the gas flow path generates a low pressure at the suction inlet;
    a collection container with a collection inlet and an outlet that is coupled to the suction inlet;
    a suction tube that has proximal and distal ends, the proximal end being connected to the collection inlet of the collection container;
    a valve located within the body for controlling gas flow through the gas flow path;
    a valve actuator for opening and closing the valve, and wherein the valve has a stem which has a pointed tip that is configured to pierce the cap of the cartridge with initial movement of the valve from a closed position and wherein, after the stem has pierced the cap of the cartridge, the valve can be opened and closed by operating said valve actuator.

2. A portable suction device according to claim 1, wherein the pointed tip has at least one passage to allow gas to flow through the tip and into the gas flow path.

3. A portable suction device according to claim 1, further comprising a filter in the gas flow path between the valve and the suction generator.

4. A portable suction device according to claim 1, wherein the cartridge has a neck having an external thread, and the body includes an internal thread to receive the external thread of the cartridge.

5. A portable suction device as claimed in claim 1 further comprising
    a sleeve which extends around the side wall of the cartridge, whereby heat is conducted from the sleeve to the cartridge as pressurized gas is discharged from the cartridge.

6. A portable suction device according to claim 5, wherein the sleeve is made of a material having a high volumetric heat capacity.

7. A portable suction device according to claim 6, wherein the sleeve is made of a material having a high thermal conductivity.

8. A portable suction device according to claim 6, wherein the sleeve is made of a material containing copper in an elastomeric matrix.

9. A portable suction device as claimed in claim 1,
    wherein the cartridge is disposed in the gas flow path such that at least a portion of the gas discharged from the suction generator is directed along the side wall of the cartridge prior to exiting the device.

10. A portable suction device according to claim 9, further comprising a shroud with an internal space within which the cartridge is disposed, the internal space forming part of the gas flow path.

11. A portable suction device according to claim 10, wherein the shroud has an exhaust end that forms the exhaust of the gas flow path.

12. A portable suction device according to claim 10, wherein the shroud projects past the base of the cartridge.

13. A portable suction device according to claim 12, further comprising a sleeve that extends around the side wall of the cartridge.

14. A portable suction device according to claim 13, wherein the device is configured such that gas discharged from the suction generator passes between the sleeve and the cartridge, and/or between the sleeve and the shroud.

15. A portable suction device according to claim 14, wherein the sleeve extends around a portion of the base, and includes an aperture through which gas can exit the sleeve.

16. A portable suction device according to claim 1, wherein the valve includes a spindle and the valve actuator can be operated, after piercing of the cap of the cartridge, to bear on the spindle to open the valve.

17. A portable suction device according to claim 16, wherein the valve includes a ball located between the stem and the spindle.

18. A portable suction device according to claim 17, further including an O-ring disposed about the spindle, and wherein when the valve is in its closed position the O-ring is compressed between the ball and a shoulder in the body.

19. A portable suction device according to claim 18, further including a spring that extends around the stem, and wherein, on release of the valve actuator, the spring urges the ball away from the stem to engage the O-ring so that it is compressed into the shoulder to thereby close the valve.

20. A portable suction device according to claim 19, further comprising a filter in the gas flow path between the valve and the suction generator.

21. A portable suction device according to claim 19, wherein the cartridge is a cylinder with a neck having an external thread, and the cap covers an opening in the neck, and the body includes an internal thread which receives the external thread of the cylinder.

22. A portable suction device as claimed in claim 21, further including a second O-ring which is compressed between the cap of the cartridge and the body to form a seal when the neck of the cartridge is threaded into the internal thread of the body.

* * * * *